United States Patent

Chedid et al.

[11] Patent Number: 6,063,380
[45] Date of Patent: May 16, 2000

[54] ENHANCED IMMUNOGENIC VACCINE

[75] Inventors: Louis Chedid; Francoise Audibert, both of Paris, France

[73] Assignee: Vacsyn S.A., Paris, France

[21] Appl. No.: 08/913,541

[22] PCT Filed: Dec. 19, 1995

[86] PCT No.: PCT/FR95/01697

§ 371 Date: Nov. 5, 1997

§ 102(e) Date: Nov. 5, 1997

[87] PCT Pub. No.: WO96/19237

PCT Pub. Date: Jun. 27, 1996

[30] Foreign Application Priority Data

Dec. 21, 1994 [FR] France ............................ 94 15425

[51] Int. Cl.$^7$ .......................... A61K 39/00; A61K 45/00; A61K 39/29; A61K 39/12

[52] U.S. Cl. .................... 424/184.1; 424/278.1; 424/204.1; 424/225.1; 424/226.1; 424/227.1; 424/196.11; 514/8; 514/894; 530/322

[58] Field of Search ............... 424/184.1, 278.1, 424/204.1, 225.1, 226.1, 227.1, 178.1, 400, 196.11; 435/69.3; 514/8, 894; 530/322

[56] References Cited

U.S. PATENT DOCUMENTS

| | | | |
|---|---|---|---|
| 5,030,720 | 7/1991 | Bertland, II et al. | 530/413 |
| 5,151,023 | 9/1992 | Kuzuhara et al. | 424/89 |
| 5,643,605 | 7/1997 | Cleland et al. | 424/489 |
| 5,728,385 | 3/1998 | Classen | 424/201.1 |

FOREIGN PATENT DOCUMENTS

| | | |
|---|---|---|
| 2533827A1 | 4/1984 | France . |
| 2672495 | 8/1992 | France . |
| WO9519777 | 7/1995 | WIPO . |

OTHER PUBLICATIONS

Jilg. Z. Gastroenterol. 35: 585–590, abstract, 1997.
Katkov. Med. Clin. North Amer. 80: 1189–1200, abstract, 1996.
Jost. Schweiz. Med. Wochenschr. 128: 1104–1109, abstract, 1998.
Ambrosch et al. Vaccine Weekly, 1 Aug. 1, abstract, 1994.
Hazama et al. Vaccine 7: 567–573, abstract, 1989.
Mahisi et al. Int. Confer. AIDS, Germany, Jun. 6–11, 9:1: p. 494, abstr. No. PO–B28–2154, 1993.
Suzuki et al. Vaccine 12: 1090–1096, abstract, 1994.
Yap et al. Vaccine 10: 439–442, abstract, 1992.
Yap et al. J. Gastroenterol. Hepatol. 10: 51–55, abstract, 1995.
Miskovsky et al. Vaccine 9: 346–350, abstract, 1991.
Coursaget et al. Vaccine 10: 379–382, abstract, 1992.
Chang et al. J. Reprod. Immunol. 9: 379–337, abstract, 1986.
Nash et al. J. Reprod. Immunol. 7:151–162, abstract, 1985.
Schutze et al. Am. J. Reprod. immunol. Microbiol. 14: 84–90, abstract, 1987.
Grob et al. Antiviral Res. 3: 43–45, 1982.
Ramasamy et al. J. Natl. Sci. Council Sri Ianka 21: 125–140, abstract, 1993.
Przewlocki et al. Biochem. Biophys. Res. Commun. 140: 557–564, abstract, 1986.
Zidek. Agents Actions 36: 136–145, abstract, 1992.
Mahisi et al. Int. J. Immunopharmacol. 11/8: 879–886, abstract, 1989.
Corradi et al. Arch. Virol. Suppl. 4: 147–153, abstract, 1992.
Parant et al. Am. J. Physiol. 247: 3 part 1: C169–C174, abstract, 1984.
AC Allison et al. Res. Immunol. 143: 519–525, 1992.
DES Stewart–Tull et al. Prog. Drug Res. 32: 305–328, 1988.
C Leclerc et al. In: RA Thompson and NR Rose (Ed), Recent Advances in Clinical Immunology, vol. 3, Churchill Livingstone, Edinburgh. pp. 187–204, 1983.
Audibert F. et al., Comptes Rendus des Seances de L'academie des Sciences Serie III: Sciences de al Vie., vol. 295, No. 10, pp. 611–614 (1982) (untranslated).
Audibert et al., Infection and Immunity, vol. 45, No. 1, pp. 261–266 (1984).

*Primary Examiner*—James C. Housel
*Assistant Examiner*—S. Devi
*Attorney, Agent, or Firm*—Birch, Stewart, Kolasch & Birch, LLP

[57] ABSTRACT

Vaccines, composed of antigens absorbed on alum or formulated in an alum-containing composition, have enhanced immunogenicity over existing vaccines. The vaccines of the invention are characterized by their combination with 2–120 μg per kg or 0.1 to 6 mg by dose, preferentially 6–60 μg per kg or 0.3 to 3 mg per dose, of a hydrosoluble muramyl peptide.

16 Claims, 1 Drawing Sheet

ENHANCED IMMUNOGENIC VACCINE

BACKGROUND OF THE INVENTION (1) Field of the Invention

The present invention relates to an improvement to vaccines containing alum in their compositions and in which the antigen can be partially or completely absorbed on alum. The improvement consists in the combining in the composition constituting these vaccines of 2 to 120 μg per kg body weight, or 0.1 to 6 mg per dose, of muramyl peptide; these vaccines thus improved have, in particular, the advantage of conferring an enhanced immunity, so that the number of injections needed for the immunization is reduced. The only immunoadjuvants currently used in human vaccines are aluminum-based compounds such as aluminum hydroxide or phosphates (alum).

(2) Description of the Related Art

This applies, in particular, to various vaccines in which the active principle consists of an antigen obtained by genetic recombination in vitro, such as Havrix, a hepatitis A vaccine in which the active principle is an antigen obtained from a hepatitis A virus strain cultured in cell culture, and containing aluminum hydroxide in the proportion of 1.5 mg per dose (0.5 mg of aluminum) and marketed by the company Smith Kline & French (6, Esplanade Charles De Gaulle, 92731 Nanterre Cedex), under the trade name Havrix. Two administrations performed at an interval of one month enable seroconversion to be induced in 98% of individuals.

Three recombinant vaccines against the hepatitis B virus are currently on the market; they are:

Genhevac B from Pasteur Mérieux Sérums et Vaccins (58, avenue Leclerc 69007 LYON FRANCE), which vaccine contains not more than 3.5 mg of aluminum hydroxide per dose, Engerix B marketed by Smith, Kline & French, containing 1.9 mg of aluminum hydroxide per dose, Recombivax HB marketed by Merck, Sharp and Dhome, containing 1.5 mg of aluminum hydroxide per dose.

The hepatitis B vaccines mentioned above are effective only after at least three injections at 0, 30 and 60 or 180 days, followed by an obligatory booster after one year; in addition, a number of subjects are poor responders or nonresponders. In the total population, they represent approximately 5%, and the capacity to obtain seroconversion depends greatly on the subject's age; it is already significantly smaller from 30–35 years onwards. Furthermore, there are groups which are especially poor responders, namely hemodialysis patients (30 to 45% of that population) and renal transplant recipients, 75 to 95% of whom do not respond to vaccines. Various investigations have studied this resistance to immunization with hepatitis B vaccines: the investigations of Stevens et al. (1), Zachoval et al. (2) and Grob PJ et al. (3) should be mentioned. This problem of lack of response to a hepatitis B vaccine becomes extremely serious in countries in which this viral infection has substantial endemic character and where approximately 5% of the population represents a considerable number of individuals; it is, in addition, especially critical in at-risk populations such as hemodialysis patients, who are rightly driven to undergo a large number of blood transfusions with the subsequent risks of viral contamination. Lastly, the fact of having to perform not less than three injections followed by a booster in order to immunize responder patients, the fourth injection coming one year after the first, represents an especially difficult and risky follow-up situation.

The problem of developing a vaccine which can, on the one hand, confer on existing nonresponders an immunization against a hepatitis virus infection, and, on the other hand, enable the number of vaccinating doses to be decreased in normal responders, permitting a follow up and a much more rigorous prophylaxis in regions where the infection is endemic or in at-risk populations, proves to be a medical necessity.

Another problem arising for the prophylaxis of hepatitis in regions where the infection is endemic is to produce a mixed vaccine against the different kinds of hepatitis, and in particular hepatitis A and B. At the present time, double vaccination against hepatitis A and B necessitates six injections, four of them for hepatitis B and two for hepatitis A; thus, the prophylaxis of hepatitis would be advantageously improved by:

improving the immunogenic power of recombinant hepatitis B vaccines, the existence of a mixed hepatitis B+hepatitis A vaccine enabling an immunization against infection by both of these viruses to be obtained in a minimum number of injections, which is impossible at the present time on account of the immunizing power of the current hepatitis B vaccines, the possibility of immunizing nonresponder subjects, the possibility of establishing a prophylaxis after 1 or 2 injections in normal responders, the possibility of establishing a prophylaxis or an immunization when the active principle of the vaccine is a hapten or, more generally speaking, a molecule which it is difficult to make immunogenic.

BRIEF SUMMARY OF THE INVENTION

Some muramyl peptides, such as murabutide or Nac-Mur-L-Ala-D-Gln n-methyl ester and murametide or Nac-Mur-L-Ala-D-Gln methyl ester have already been developed in preclinical trials of efficacy and of acute, subacute and chronic toxicity, as well as in phase 1 trials in man; excellent tolerance was demonstrated following an administration to more than 200 subjects for murabutide and 50 subjects for murametide. In order to solve the problem, set out above, of improving vaccines, in particular the existing ones against hepatitis B, or of creating a mixed hepatitis vaccine displaying enhanced immunogenicity, making it possible to reduce the number of injections on the one hand and to protect against infection subjects who were hitherto nonresponders with the traditional vaccines on the other hand, the inventors had the idea of combining muramyl peptides with existing vaccines in which the antigens are formulated in the presence of alum. The adjuvant doses contain an amount between 2 and 120 μg per kg body weight, or 0.1 to 6 mg per single dose, of water-soluble muramyl peptide of formula:

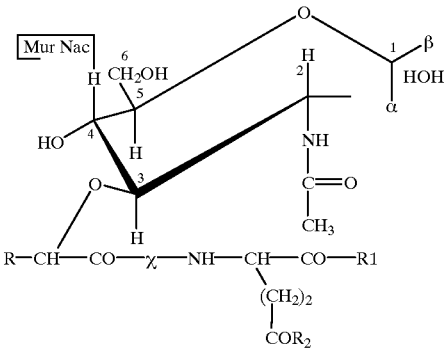

(1)

in which the group R is a hydrogen or a methyl group, X is an L-alanyl or L-threonyl residue and R1 and R2 are, independently of one another, hydroxyl, amino or $O(CH_2)_xH$ groups with $x=1, 2, 3$ or 4, on the understanding that, when X is an L-alanyl residue, at least one of these two groups R1 and R2 is always an $O(CH_2)_xH$ group as defined above. Still more especially, the muramyl peptide of the invention is one of the ones corresponding to the above formula in which the group R is a methyl group and the group R2 is an NH2 group.

In this formula, the preferred MDP derivatives are murabutide, murametide, muradimetide or MDP-threonyl. MDP an abbreviation of Muramyl-dipeptide. Another preferred MDP derivative is $N^\alpha$(NAcMur)-L-Lys-D-isoGln-sn-glyceryl dipalmitoyl (abbreviated as MDP(L-Lys)-snGDP) which has the property of being water-soluble.

The preferred adjuvant doses are 6 to 60 μg per kg body weight, equivalent, for a person weighing 50 kg, to 0.3 to 3 mg per vaccinating dose.

DETAILED DESCRIPTION OF THE INVENTION

Figure 1:
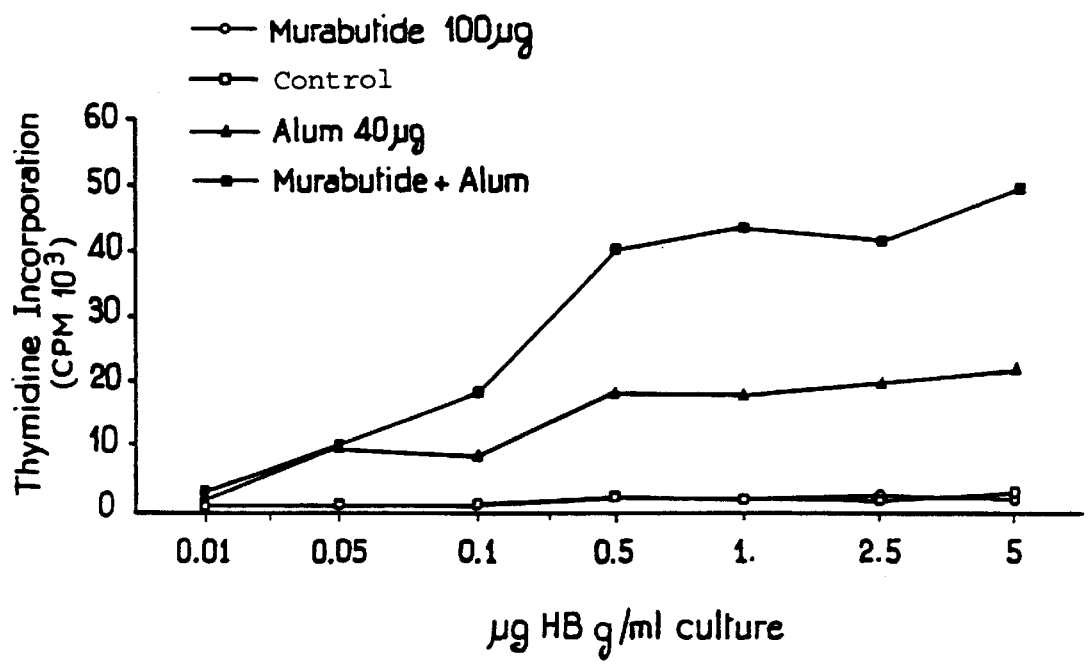
FIG. 1 shows the proliferation of T cells, measured by incorporation of tritiated thymidine, as a response to increasing concentrations of hepatitis antigens.

The combination of an MDP derivative as described above with a hepatitis B vaccine containing antigens obtained by genetic recombination and absorbed on aluminum hydroxide (alum) is especially advantageous:

either for obtaining a recombinant hepatitis B vaccine which is effective in two injections instead of the three or four which are necessary at the present time in the existing vaccines, or for formulating a mixed vaccine, in particular hepatitis A+hepatitis B, enabling a population to be vaccinated with a restricted number of injections, or for immunizing populations which hitherto consisted of subjects who were nonresponders to the existing vaccine, and in particular hemodialysis patients or renal transplant recipients.

Hence the invention relates to hepatitis vaccines absorbed on alum and improved by the combining of 2 to 120 μg per kg body weight, or 0.1 to 6 mg per vaccinating dose, preferably of 6 to 60 μg per kg or 0.3 to 3 mg per dose, either of a compound of formula (I) or MDP-Lys-GDP.

The vaccines of the invention can, in particular, be improved with a derivative of formula (I) in which the group R is a methyl group, and the group $R_2$ is an $NH_2$ group, and still more especially murabutide, murametide, muradimetide, MDP-threonine or MDP-Lys-GDP.

A vaccine according to the invention is characterized in that it contains a recombinant hepatitis B antigen; the vaccine can be:

either a hepatitis B vaccine or a mixed hepatitis A+B vaccine or any other mixed vaccine, provided it contains the recombinant hepatitis B antigen.

The hepatitis B vaccines of the invention preferably contain as vaccinating antigen the S region and all or part of the pre-S region, especially the pre-S2 region, of the surface antigen of the virus.

The invention also relates to a process for manufacturing a vaccine displaying enhanced immunogenicity, characterized in that said vaccine consists of antigens absorbed on alum or formulated in a composition containing alum, and to which are added 2 to 120 μg per kg body weight, or 0.1 to 6 mg per vaccinating dose, preferably between 6 and 60 μg per kg or 0.3 to 3 mg per vaccinating dose, of muramyl peptide of formula (I) above or MDP-Lys-GDP.

Advantageously, the muramyl peptide derivative is chosen from murametide, murabutide, muradimetide and threonyl MDP. The process of the invention enables improved vaccinating compositions against hepatitis B to be manufactured, and also makes it possible to manufacture mixed vaccinating compositions enabling a population to be vaccinated both against the hepatitis B virus, or any mixed vaccine, provided it contains the recombinant hepatitis B antigen, and in particular a mixed hepatitis A+B or hepatitis A+B+C vaccine, provided their formulation contains alum.

Lastly, the invention relates to the use of 2 to 120 μg per kg body weight, or 0.1 to 6 mg per dose, and preferably of 6 to 60 μg per kg weight or 0.3 to 3 mg per vaccinating dose, of a muramyl peptide of formula (1) above or of MDP-Lys-GDP, for improving the immunogenicity of a vaccine composed of recombinant antigens absorbed on alum or formulated in a composition containing alum. This use applies most especially to the recombinant hepatitis B vaccine, or to a mixed vaccine, provided it contains the recombinant hepatitis B antigen, and in particular a mixed hepatitis A+B or hepatitis A+B+C vaccine, provided their formulation contains alum. In this use, murabutide, murametide, muradimetide and threonyl MDP are more especially preferred. Vaccination against small molecules such as haptens is problematical in view of their low immunocenicity. In order to stimulate the latter, the hapten may be coupled to a carrier molecule; however, there is a risk of producing a response against the carrier molecule at the expense of the hapten. The use of 0.1 to 6 mg per vaccinating dose, and preferably 0.3 to 3 mg, of muramyl peptides of formula (1) or of MDP-Lys-GDP in the manufacture of a vaccine comprising at least one hapten as vaccinating antigen also forms part of the invention, as do the vaccines containing as immunogen at least one hapten coupled or not coupled to a carrier molecule.

The vaccines comprising at least one hapten and at least one recombinant antigen, one of them being absorbed on alum, combined with a muramyl peptide derivative, form part of the invention.

As shown in the nonlimiting examples below and the FIGURE, the combination of a derivative of formula (I) or of MDP-Lys-GDP with alum in a vaccinating composition has the effect of inducing:

1) specific T cells: it is known that the T cells capable of proliferating in the presence of the antigen, which have hence been sensitized specifically to the latter, are the cells responsible for establishment of the immune memory. It is by virtue of these cells that the vaccinated individual can respond immediately to an attack by the virus against which he or she has sought to acquire protection. Hence it is of the utmost importance to provide a vaccine capable not only of inducing antibodies on a long-term basis, but also memory T cells. This enables the vaccinated individuals to benefit from two lines of immune defenses.

2) an enhanced synthesis of specific antibodies: this enhanced synthesis takes place at the expense of the synthesis of IgE, which is known for the risk it runs of causing reactions of allergic nature. The examples which follow illustrate the capacity of the various muramyl peptides to give a synergistic effect with alum.

3) of inducing a specific response against a hapten used as immunogen in a vaccine. In all of the foregoing, these effects are induced more 15 especially when the weight/weight ratio of the alum to the muramyl peptides remains within a certain range, which is from 0.15 to 35 and preferably 1 and 10. This ratio is calculated on the following amounts per vaccinating dose:

1 to 3.5 mg of alum,
0.1 to 6 mg of muramyl peptide.

The FIGURE and the examples below illustrate the improvement provided by the invention, without limiting the latter.

EXAMPLE 1

Increase in Specific T Cells

The surprising effect obtained, and in particular that of rendering immunogenic a vaccine which is currently non-immunogenic in some categories of the population, may be linked to the specific increase in a proliferative response of the T cells. This increase in the number of T cells sensitized to the antigen also makes it possible to evaluate the level of immunological memory which has been induced. This is illustrated by the following experiment:

Mice were sensitized to the hepatitis B virus surface antigen; T cell proliferation was measured by incorporation of tritiated thymidine after incubation with the antigen present in the culture medium. FIG. 1 shows this response in four particular cases as regards the adjuvant used: a) no adjuvant (open squares); b) alum alone at a dose of 40 µg (black triangles); c) murabutide alone at a dose of 100 µg (open circles); and d) the combination of murabutide at 100 µg and alum at 40 µg (black squares). The results seen in this FIGURE show that alum alone is capable of increasing T cell proliferation, but that the combination with murabutide induces a response which is 3 times as high as that obtained in the presence of alum alone, as shown by measuring the incorporation of tritiated thymidine (45,000 CPM versus 15,000).

The protocol of this experiment is as follows: Balb/C mice received 5 µg of HBS antigens by subcutaneous injection at the base of the tail in 0.1 ml of PBS buffer with or without adjuvants. Two weeks later, the T lymphocytes were cultured in PBS or with increasing doses of HBS antigens, as shown as abscissae. After five days, the proliferative response was measured by incorporation of tritiated thymidine. The results in FIG. (1) are shown as the average number of counts per minute in triplicate.

EXAMPLE 2

Effect of Murabutides on the Synthesis of Specific Antibodies

The effect of adding an MDP derivative of formula (I) or MDP-Lys-GDP in the presence of alum can also be demonstrated by a relative increase in the response in terms of specific immunoglobulins following the vaccinating effect. A recombinant hepatitis B vaccine absorbed on alum was used. Various experiments were carried out, either on Swiss mice or on Balb/C mice; they demonstrate consistently the effect of adding murabutide on the hepatitis B vaccines absorbed on alum. Furthermore, these experiments showed reproducibly that the level of the IgG type antibodies is increased while that of the IgE antibodies is decreased, indicating that the use of the muramyl peptide enabled the allergic type risks of the vaccine to be reduced.

a) Two groups of 40 mice were immunized with two injections of vaccine at an interval of 1 month in the presence or absence of murabutide. 70% of the animals treated with the murabutide have antibody titers (measured using the EIA AUSAB kit, Abbot Laboratories) above 50 mIU, this being the case for more than 4 months, whereas only 25% of the controls show this titer, which is, furthermore, transient since it has already slumped after 2 months.

b) Table 1 shows the aggregate of the results obtained in 6 similar experiments. The anti-HBS antibody titers are expressed in milliunits per ml as a function of time. One control group received two vaccinations, a second control group received three vaccinations and an experimental group received two injections of the vaccine with the addition of murabutide.

TABLE 1

| Immunization | Antibodies D20 | Antibodies D40 | Antibodies D70 | Antibodies D140 |
| --- | --- | --- | --- | --- |
| HBS + alum 2 injections | 30 | 120 | 170 | 250 |
| HBS + alum 3 injections | 30 | 120 | 950 | 1200 |
| HBS + alum + murabutide 2 injections | 40 | 300 | 1500 | 2600 |

The Swiss mice (8 per group) received by subcutaneous injection 1 µg of HBS antigen and 135 µg of alum with or without 100 µg of murabutide on day 0. They receive a booster injection on day 30. On day 60, only the control group with alum and without murabutide receives a third injection. The antibodies are measured by EIA.

It is clearly apparent that the animals which have received only two vaccinations with the murabutide have an antibody titer higher than that of the animals which have received three injections of the vaccine alone; as regards the controls which have received two injections, the titer of their antibodies remains modest and decreases rapidly.

These experiments show that the improvement of the existing hepatitis B vaccines by adding a muramyl peptide as defined in the formula (I), and more especially murametide, murabutide, muradimetide or MDP-Lys-GDP, can make it possible to solve a problem of the magnitude of the one arising, namely to vaccinate responder individuals in 1 or 2 injections and to be able to vaccinate populations which are currently resistant to vaccination, either naturally or following treatments such as hemodialysis or a transplantation.

EXAMPLE 3
Effect of Murametide on the Synthesis of Specific Antibodies

Similar results were obtained using murametide and muradimetide, as is shown by the following experiments:

Balb/C mice (8 per group) received by subcutaneous injection 1 μg of HBS antigen and 135 μg of alum with or without 100 μg of murametide on days 0 and 30. The antibodies are measured by ELISA on days 23 and 54.

TABLE 2

| Immunization | Antibodies D28 | Antibodies D54 |
| --- | --- | --- |
| HBS + alum (Control) | 35 | 520 |
| HBS + alum + murametide | 245 | 2700 |

EXAMPLE 4
Effects of Muradimetide and of MDP-Lys-GDP on the Synthesis of Specific Antibodies In a separate experiment performed on Swiss mice receiving the same doses of vaccine and of adjuvant as those mentioned in Example 3, muradimetide and MDP-Lys-GDP were capable of inducing primary and secondary responses 3 to 4 times as high as those of the controls.

TABLE 3

| Immunization | Antibodies D21 | Antibodies D80 |
| --- | --- | --- |
| HBS + alum (Control) | 10 | 700 |
| HBS + alum + muradimetide | 60 | 2250 |
| HBS + alum + MDP-Lys-GDP | 35 | 2600 |

The invention may also be applied to other antigens as shown in Example 5.

EXAMPLE 5
Efficacy of the Combination of Murabutide and Alum for Increasing the Humoral Response to a βHCG Vaccine (βHCG Conjugated to Tetanus Toxoid)

The antigen is a conjugate containing β chain of chorionic gonatropic hormone (βHCG) coupled to tetanus toxoid (TT) (20% of βHCG in the conjugate). This conjugate is designed for use as a contraceptive vaccine, since anti-HCG antibodies block the implantation and development of the egg.

Balb/C mice (groups of 8 females) received subcutaneously 10 μg of βHCG conjugated to the toxoid. The antigen was administered either alone or in an emulsion of Freund's incomplete (FIA) or with alum (200 μg) or with murabutide (100 μg) or with alum and murabutide. The antibodies which combine with HCG were measured by ELISA on day 20. The βHCG-TT conjugate is administered absorbed on alum, and the results obtained shown in Table 4 below.

TABLE 4

Efficacy of the combination of murabutide and alum for increasing the humoral response to a βHCG vaccine (βHCG conjugated to tetanus toxoid)

| Adjuvant | Antibody response on day 20 |
| --- | --- |
| None (Control) | 12,500 |
| FIA (oil) | 26,000 |
| Alum | 15,500 |

TABLE 4-continued

Efficacy of the combination of murabutide and alum for increasing the humoral response to a βHCG vaccine (βHCG conjugated to tetanus toxoid)

| Adjuvant | Antibody response on day 20 |
| --- | --- |
| Murabutide | 53,000 |
| Alum + murabutide | 200,000 |

It is clear that, after a single injection of vaccine absorbed on alum and with murabutide as adjuvant, very high titers of antibodies which recognize the HCG hormone are obtained. Separate experiments showed us that these antibodies are biologically active and neutralize the activity of HCG. The data obtained in Example 5 are strongly backed up by those described in Example 6 below:

EXAMPLE 6
Hapten-carrier System in Which the Muramyl Peptide/Alum Combination Enables High Antibody Titers but, Most Especially, Biologically Active Antibodies to be Obtained, an Essential Result for the Success of a Vaccination In Example 6, the objective of the vaccination is to obtain antibodies capable of neutralizing the biological activity of a hormone. This hormone is a decapeptide produced by the hypothalamus and is absolutely devoid of immunogenicity. Even after coupling to a "carrier" molecule, it is incapable after several injections of inducing the production of a significant level of antibodies.

The hormone in question, called luteineizing hormone-releasing hormone or LH-RH, is synthesized at central level in the hypothalamus and, following a cascade of interactions, it controls completely the synthesis of the sex hormones in the male or the female, and especially the production of testosterone. Consequently, LH-RH controls the development and functioning of the testes, the prostate and the seminal vesicles. If the LH-RH level is low, but, most especially as far as we are concerned, if its activity is neutralized by biologically active antibodies, there is a decrease in the level of circulating testosterone and involution of the sex organs. It has been shown by many authors, and in all the species tested (mouse, rat and guinea pig, livestock), that an LH-RH conjugate with tetanus toxoid (LH-RH-TT) enables biologically active antibodies (that is to say ones capable of neutralizing LH-RH activity) to be obtained only if it is administered combined with a very potent adjuvant preparation. The preparation generally used is Freund's complete adjuvant (FCA), which is also well known to have substantial side effects that absolutely prohibit its use in human or veterinary medicine. Now, there are cancers (prostate cancers) whose development is linked to the secretion of testosterone. It is hence important, if it is desired to develop an immunological treatment by vaccination for this type of cancer, to find an effective formulation of LH-RH which is compatible with a clinical administration. The same need exists if it is desired to use an anti-LH-RH vaccine in order to produce a castration effect in animals. The muramyl peptide/alum combination meets these requirements, as demonstrated in the example which follows.

In the experiment described, male Sprague-Dawley breed rats weighing 250 g received three injections of LH-RH-TT conjugate (50 μg) at 30-day intervals. This conjugate was administered:

a) alone, b) in an emulsion of FCA, c) mixed with 100 μg of murametide, d) absorbed on alum (400 μg), e) absorbed on alum and with the addition of murametide. The anti-LH-RH antibodies are measured at various times during the experiment, as are the blood testosterone levels. After 130 days, the animals are sacrificed and their sex organs removed for histological study. The results of a characteristic experiment are recorded in Table 5 below. They show that the highest antibody levels were obtained in the group receiving FCA, but also in the last group (alum/murametide). Still more importantly, it is only in these two groups that a considerable fall in the testosterone level and an involution of the sex organs are observed.

The results of the murametide/alum combination on the production of biologically active anti-LH-RH antibodies are shown in Table 5 below.

Herwig, W., Iselin, H. Descoeudres, C. Immunogenicity of hepatitis B subunit vaccine in hemodialysis and in renal transplant recipients. Antiviral Research 1983, 3: 43–52.

What is claimed is:

1. A vaccine composition comprising:
   (1) antigens absorbed on alum or formulated in a composition comprising alum; and
   (2) 2 to 120 μg per kg body weight or 0.1 to 6 mg per vaccinating dose of a muramyl peptide selected from the group consisting of murabutide, murametide and muradimetide, wherein the ratio of the amount by weight of alum to the amount by weight of said muramyl peptide is 1.35 to 4.

2. The vaccine according to claim 1, wherein the vaccinating dose contains 6 to 60 μg per kg body weight or 0.3 to 3 mg per vaccinating dose of said muramyl peptide.

TABLE 5

| | Titer of anti-LR-RH antibodies obtained by Elisa on days | | | | Testosterone level in ng/ml serum on days | | | | Histology of the organs θ | | | | | |
|---|---|---|---|---|---|---|---|---|---|---|---|---|---|---|
| | | | | | | | | | Testes | | Prostate | | Seminal vesicles | |
| | | | | | | | | | Average weight | Number of animals | Average size | Number of animals | Average size | Number of animals |
| IMMUNIZATION | 20 | 40 | 70 | 130 | 20 | 40 | 70 | 130 | (g) | affected | (mm) | affected | (mm) | affected |
| LH-RH-TT | <1000 | 1200 | 3800 | 3200 | 3.5 | 1.85 | 1.50 | 1.10 | 2 | 0/6 | 2.67 | 0/6 | 6.5 | 0/6 |
| LH-RH-TT + FCA | 1000 | 7500 | 25,000 | 22,000 | 2.80 | 0.60 | 0.20 | 0.10 | 0.4 | 5/6 | NT° | | NT | |
| LH-RH-TT + murametide | <1000 | 1100 | 3500 | 3500 | 2.95 | 1.50 | 1.35 | 1.5 | 1.95 | 0/6 | NT | | NT | |
| LH-RH-TT + alum | 1000 | 3450 | 13,000 | 7100 | 2.70 | 0.70 | 0.70 | 0.80 | 1.55 | 1/6 | 2.8 | 1/6 | 5.6 | 1/6 |
| LH-RH-TT + alum + murametide | 1300 | 9800 | 28,000 | 15,000 | 2.55 | 0.50 | 0.07 | 0.14 | 0.5 | 5/6 | 2.08 | 5/6 | 3.6 | 5/6 |

θThe organs were removed, then weighed or measured. After undergoing appropriate preparation, they were subjected to anatomopathological examinations. The lesions observed in the affected animals are characteristic of an absence of stimulation by testosterone.
°NT = not tested.

Similar results were obtained using murabutide or MDP-lys-GDP combined with alum.

Examples 5 and 6 described above show that the combination of muramyl peptides with antigens absorbed on alum is especially advantageous in the case where the vaccinating principle is a hapten necessitating coupling to a carrier molecule. This case may arise when the vaccinating principle is a peptide, a poorly immunogenic protein or a sugar.

On the basis of these results, a person skilled in the art can readily envisage the production of polyvalent vaccines containing, besides a hapten, another vaccinating antigen, provided that one of the vaccinating molecules is absorbed on alum and that the vaccinating combination contains an MDP derivative according to the invention.

REFERENCES (1) Stevens, C. E., Goodman, A. I., Szmuness, W., Weseley, S. A., Fotino, M. Hepatitis B. vaccine: immune responses in haemodialysis patients The Lancet 1980, ii; 1211–1213.

(2) Zachoval, R., Frosner, G., Deinhardt, F. Impfung gegen Hepatitis B. Ergebnisse einer Immunogenitätsstudie [Vaccination against hepatitis B. Results of an immunogenicity study]. Münchner medizinische Wochenschrift 1981, 123: 1506–1508.

(3) Grob, P. J., Binswanger, U., Zaruba, K., Joller-Jemelka, H. I., Schmid, M., Häcji, W., Blumberg, A., Abplanalp, A., 3. The vaccine according to claim 1, wherein said antigens absorbed on said alum or formulated in a composition containing said alum consist of the S region and all or part of the pre-S region of the Hepatitis B virus surface antigen.

4. The vaccine according to claim 1, wherein said antigens absorbed on said alum or formulated in a composition containing said alum consist of LH-RH antigens.

5. The vaccine according to claim 1, wherein said antigens absorbed on said alum or formulated in a composition containing said alum comprise βHCG antigens.

6. The vaccine according to claim 1, wherein said antigens absorbed on said alum or formulated in a composition containing said alum comprise hepatitis A and B antigens.

7. The vaccine according to claim 1, wherein said antigens absorbed on said alum or formulated in a composition containing said alum are further coupled to a carrier molecule.

8. A process for manufacturing a vaccine comprising the step of:

absorbing antigens on alum or formulating antigens in a composition containing alum wherein the composition consists of 2 to 120 μg per kg body weight or 0.1 to 6 mg per vaccinating dose of a muramyl peptide selected from the group consisting of murabutide, murametide and muradimetide, wherein the ratio of the amount by weight of alum to the amount by weight of said muramyl peptide is 1.35 to 4.

9. The process according to claim 8, wherein the vaccinating dose contains 6 to 60 μg per kg body weight or 0.3 to 3 mg per vaccinating dose of said muramyl peptide.

10. The process according to claim 8 or claim 9 wherein said vaccine is selected from the group consisting of a hepatitis B vaccine, a mixed vaccine comprising antigens specific to the hepatitis B virus and a mixed vaccine comprising haptens coupled or not coupled to a carrier molecule.

11. The process according to claim 10, wherein said antigens specific to the hepatitis B virus are recombinant antigens.

12. An immunizing method comprising:

administering to a patient 2 to 120 μg per kg body weight or 0.1 to 6 mg per vaccinating dose of a muramyl peptide in a vaccine composition comprising antigens absorbed on alum or formulated in a composition containing alum, wherein said muramyl peptide is selected from the group consisting of murabutide, murametide and muradimetide and the ratio of the amount by weight of alum to the amount by weight of said muramyl peptide is 1.35 to 4.

13. An immunizing method comprising:

administering to a patient 2 to 120 μg per kg body weight or 0.1 to 6 mg per vaccinating dose of a muramyl peptide in a vaccine composition comprising haptens coupled or not coupled to a carrier molecule, the vaccine being absorbed on alum or formulated in a composition containing alum, wherein said muramyl peptide is selected from the group consisting of murabutide, murametide and muradimetide, wherein the ratio of the amount by weight of alum to the amount by weight of said muramyl peptide is 1.35 to 4.

14. The method according to claim 13, wherein said vaccine composition comprises a recombinant antigen.

15. A vaccine composition comprising:

(1) antigens absorbed on alum or formulated in a composition comprising alum wherein said antigens are selected from the group consisting of hepatitis B antigens, βHCG antigens and LH-RH antigens; and (2) 2 to 120 μg per kg body weight or 0.1 to 6 mg per vaccinating dose of a muramyl peptide selected from the group consisting of murabutide, murametide and muradimetide, wherein the ratio of the amount by weight of alum to the amount by weight of said muramyl peptide is 1.35 to 4.

16. An immunizing method comprising:

administering to a patient 2 to 120 μg per kg body weight or 0.1 to 6 mg per vaccinating dose of a muramyl peptide selected from the group consisting of murabutide, murametide and muradimetide in a vaccine composition comprising antigens absorbed on alum or formulated in a composition containing alum wherein said antigens are selected from the group consisting of hepatitis B antigens, βHCG antigens and LH-RH antigens, wherein the ratio of the amount by weight of alum to the amount by weight of said muramyl peptide is 1.35 to 4.

* * * * *